United States Patent
Zhang et al.

(10) Patent No.: US 8,275,092 B1
(45) Date of Patent: Sep. 25, 2012

(54) THREE-DIMENSIONAL MAPPING BASED ON SCATTERED PENETRATING RADIATION

(75) Inventors: Ming Zhang, Wayland, MA (US); Omar Al-Kofahi, Woburn, MA (US); Wamiq Ahmed, Woburn, MA (US)

(73) Assignee: American Science and Engineering, Inc., Billerica, MA (US)

( * ) Notice: Subject to any disclaimer, the term of this patent is extended or adjusted under 35 U.S.C. 154(b) by 265 days.

(21) Appl. No.: 12/793,210

(22) Filed: Jun. 3, 2010

Related U.S. Application Data

(60) Provisional application No. 61/186,976, filed on Jun. 15, 2009.

(51) Int. Cl.
*G01N 23/04* (2006.01)
(52) U.S. Cl. .......................... 378/57; 378/62
(58) Field of Classification Search .............. 378/62, 378/57; 382/131
See application file for complete search history.

(56) References Cited

U.S. PATENT DOCUMENTS 7,400,701 B1    7/2008   Cason .............................. 378/57

OTHER PUBLICATIONS

Singh, et al., "Explosives Detection Systems (EDS) for Aviation Security: A Review", PANN Research, Dept. of Computer Science, University of Exeter, Exeter EX4 4PT, UK, pp. 1-62, 2003.
Benosman, et al, *Panoramic Vision*, 2001 (Entire Book).

*Primary Examiner* — Courtney Thomas
(74) *Attorney, Agent, or Firm* — Sunstein Kann Murphy & Timbers LLP

(57) ABSTRACT

Methods for a tangible image of an inspected object. An object is illuminated with at least two sources of penetrating radiation that generate respective pencil beams and define respective viewing points and view planes. Post-interaction penetrating radiation due to the respective sources is used to generate signals based on respective views of the inspected object, and thus derive information with respect to a dimension transverse to the first view plane based on the second signal. A tangible image of the inspected object is then displayed depicting information with respect at least to the first view plane and the transverse dimension.

6 Claims, 6 Drawing Sheets

THREE-DIMENSIONAL MAPPING BASED ON SCATTERED PENETRATING RADIATION

The present application claims priority from U.S. Provisional Patent Application Ser. No. 61/186,976 filed Jun. 15, 2009, and incorporated herein by reference.

TECHNICAL FIELD

The present invention relates to systems and methods for assisting the operator of a backscatter inspection system to identify regions of objects that have a high probability of being potential threats by presenting to the operator an image that is more readily interpreted.

BACKGROUND OF THE INVENTION

X-ray systems are routinely used for screening vehicles and cargo crossing international borders, as well as for screening passengers and baggage. Such systems are based on the interaction of penetrating radiation with contents of a vehicle or a cargo enclosure. Current systems allow a human operator to view the contents of a vehicle on a display and flag any anomalies. Manual inspection of X-ray images makes this a slow process. Due to the large number of vehicles crossing international borders there is a pressing need for developing systems and methods that can assist the operator in screening vehicles.

One modality of X-ray inspection that has proven highly efficacious in a multitude of circumstances is that of scatter imaging, or, more particularly, backscatter imaging. One backscatter imaging system, in the context of which the present invention may be advantageously applied, is fully described in U.S. Pat. No. 7,400,701 (to Cason), issued Jul. 15, 2008, and incorporated herein by reference.

SUMMARY OF EMBODIMENTS OF THE INVENTION

In accordance with various embodiments of the present invention, methods are provided for creating a tangible image of an inspected object. The methods include steps of:
  illuminating the object with a first source of penetrating radiation, the first source of radiation generating a pencil beam that penetrates the inspected object to a significant depth and that defines a first viewing point;
  illuminating the object with a second source of penetrating radiation, the second source of radiation generating a pencil beam that penetrates the inspected object to a significant depth and that defines a second viewing point;
  detecting post-interaction penetrating radiation due to the first source and generating a first signal based on a first view of the object, characterized by a first view plane, of the inspected object;
  detecting post-interaction penetrating radiation due to the second source and generating a second signal based on a second view of the inspected object;
  deriving information with respect to a dimension transverse to the first view plane based on the second signal; and
  displaying a tangible image of the inspected object depicting information with respect at least to the first view plane and the transverse dimension.

In accordance with other embodiments of the invention, the method may also have a step of segmenting the first view of the object. Either step of illuminating may include illuminating with x-ray radiation. An additional step may be provided of constructing a three-dimensional surface of the object for display as the tangible image.

In accordance with various embodiments, the object of inspection may be a vehicle, and it may be a person.

BRIEF DESCRIPTION OF THE DRAWINGS

The foregoing features of the invention will be more readily understood by reference to the following detailed description taken with the accompanying drawings:

FIG. 3($a$) is a side view after segmentation; FIG. 3($b$) is the side view after refined segmentation; FIG. 3($c$) is a top view after segmentation; and FIG. 3($d$) is the top view after refined segmentation.

DETAILED DESCRIPTION OF EMBODIMENTS OF THE INVENTION

Definitions

As used herein and in any appended claims, a "tangible image" refers to a depiction of an object that is available to be apprehended by one of the human senses, typically vision.

A "viewing point" refers herein to a point in space from which a view or an image (tangible or intangible) appears to have been derived. The viewing point need not correspond to the actual placement of one or more detectors. Indeed, in the case of backscatter imaging using a scanned pencil beam to define an instantaneous locus of illuminated regions on the target, the effective viewing point refers to the point from which the illuminating penetrating radiation appears to emanate.

A "significant penetration depth," in the context of scatter-based inspection, refers to a depth that is at least ten times the lateral resolution of an illuminating beam, typically a depth of at least several centimeters. "Penetrating radiation" refers either to waves or to particles that penetrate a medium to a significant penetration depth. Thus, for example, visible light incident on an opaque medium such as a metal, attenuated exponentially within a skin depth on the order of the wavelength of light, is not penetrating radiation within the sense required by the present application.

"Post-interaction penetrating radiation" refers to the result of penetrating radiation having been incident upon an inspected object and interacting with the medium comprising the object, via any physical mechanism, and having given rise to further penetrating radiation, whether through mechanisms of coherent or incoherent scattering, etc.

When incident radiation interacts with an object, it may give rise to scattered radiation, whether coherent or incoherent. Detection, in turn, of the scattered radiation, gives rise to one or more scatter signals.

In accordance with various embodiments of the present invention, a system is described in which scatter signals derived from multiple viewing points are combined to generate a single image that may be advantageously viewed by an operator. Such a system employs a plurality of sources of penetrating radiation, and at least one scatter detector. One or more scatter detectors may detect radiation for each source of penetrating radiation after scattering interaction of the radiation with an inspected object. That is to say that, within the scope of the present invention, scatter detectors may be common to more than one source of penetrating radiation. Sources of penetrating radiation, and various exemplary detector configurations are described and depicted in U.S. Pat. No. 7,400,701 (to Cason), which is incorporated herein by reference, without limitation. All other types of sources and configurations are within the scope of the present invention, as well.

Figure 1:
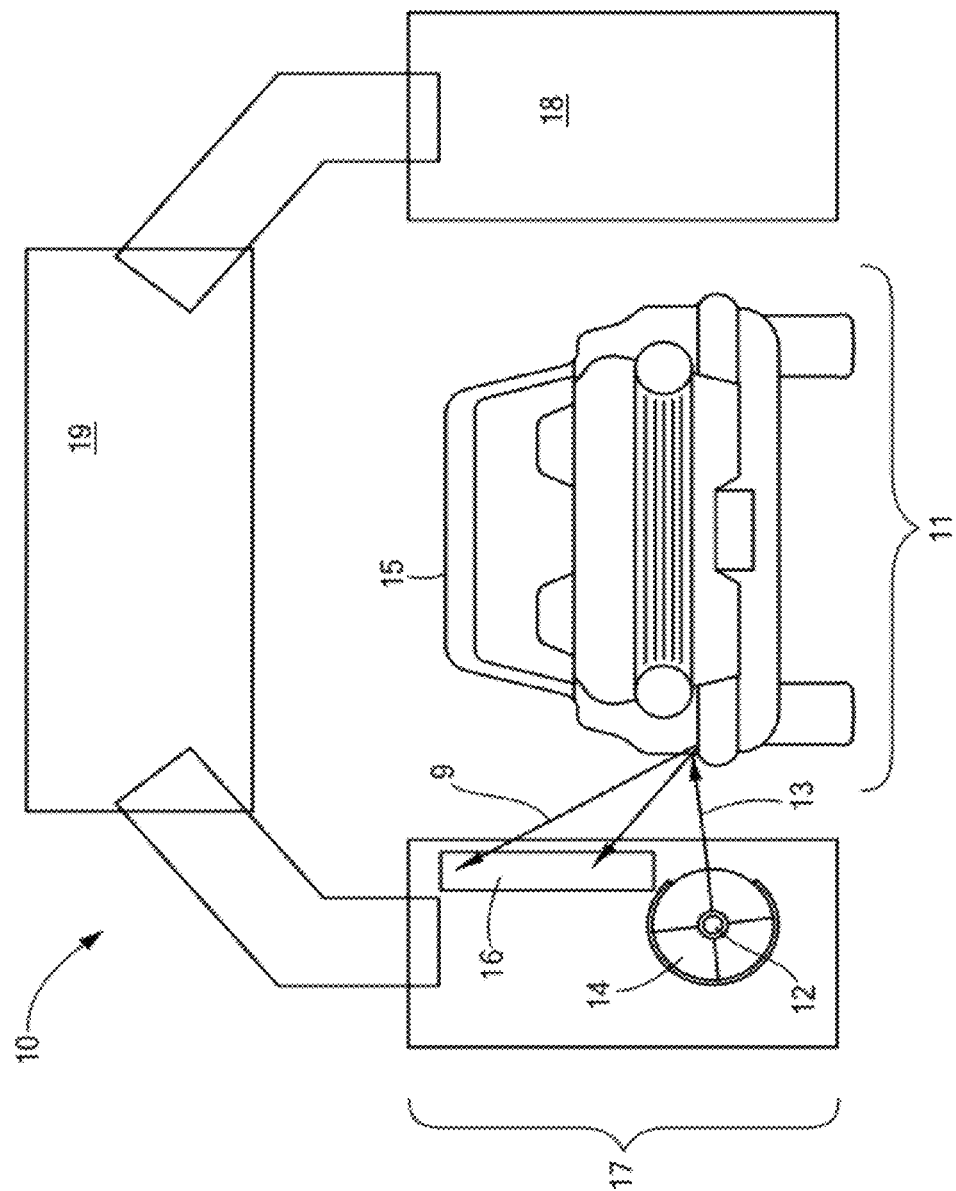
FIG. 1 shows a prior art inspection system, with imaging modules to either side, and above, an inspected object.

Referring to a prior art inspection system 10 depicted in FIG. 1, the conjunction of a source 12 of penetrating radiation 13, along with a beam-forming configuration of any sort (such as a collimator, for example), and a scanner 14 (such as a chopper wheel, for example) for scanning the penetrating radiation across an inspected object 15 (shown, here, as a car) and, further, along with one or more detectors 16 for detecting post-interaction radiation scattered by the inspected object, may be referred to, herein, as a "scatter imaging module" 17. By way of example, and without limitation, the present description may refer to a scatter imaging module as a "backscatter imaging module." It is to be understood that the term "inspected object" includes not only inanimate objects, such as vehicles, but may also include inspected persons.

In preferred embodiments of the invention, x-ray energies are employed that penetrate the exterior surface of the inspected object to a significant penetration depth, typically at least several centimeters.

Prior art system 10 is one in which the present invention may be employed advantageously, where scatter imaging modules are provided on the left 17, right 18, and top 19 of the inspected object 15. The system depicted has three backscatter imaging modules (left, right, and top). Each imaging module is complete with X-ray source 12, beam-forming configuration, and detectors 16. The three sources are typically temporally interlaced such that only one X-ray pencil beam 13 is active in the tunnel 11 (i.e., the volumetric region encompassing the inspection capability) at any point in time, and the inspection system generates backscatter images from these three sides. Additionally, forward scatter images may be provided from the left and right sides.

In the context of the present invention, application of the present methods to an inspection system in which three backscatter images are derived is used solely by way of example. It should be noted that the methods and techniques described herein are equally applicable to systems that create either fewer or more than three images.

A scatter detector signal may be processed, using known processing techniques, to form an array of pixels that is denoted as a "view," representing an image of the inspected object from a particular viewing point. The image designated generally by numeral 30 in FIG. 3(*a*) is an example of such a view. Such known processes include any manner of filtering, whether on a pixel-by-pixel basis or incorporating neighboring pixels. Additionally, processing by means of segmentation is also included within the scope of the present invention. Segmentation refers to partitioning a view so as to identify discrete subsets of pixels that share some common characteristic, such as commonly falling within the boundaries of an identified object, such as a vehicle or a component, such as a tire. References describing such techniques include:

1. "Explosives detection systems (EDS) for aviation security," Singh et al., Signal Processing, 83 (2003), pp. 31-55;
2. "Computer and Robot Vision," Haralick et al., Prentice Hall, (2002);
3. "Advances in Image and Video Segmentation," Yu-jin Zhang, IRM Press, (2006).

Each of the foregoing references is incorporated herein by reference.

In accordance with one embodiment of the present invention, a plurality of backscatter imaging modules are employed, each associated with a viewpoint, and each generating a backscatter view. Multiple segmented views are automatically registered together.

Figure 2:
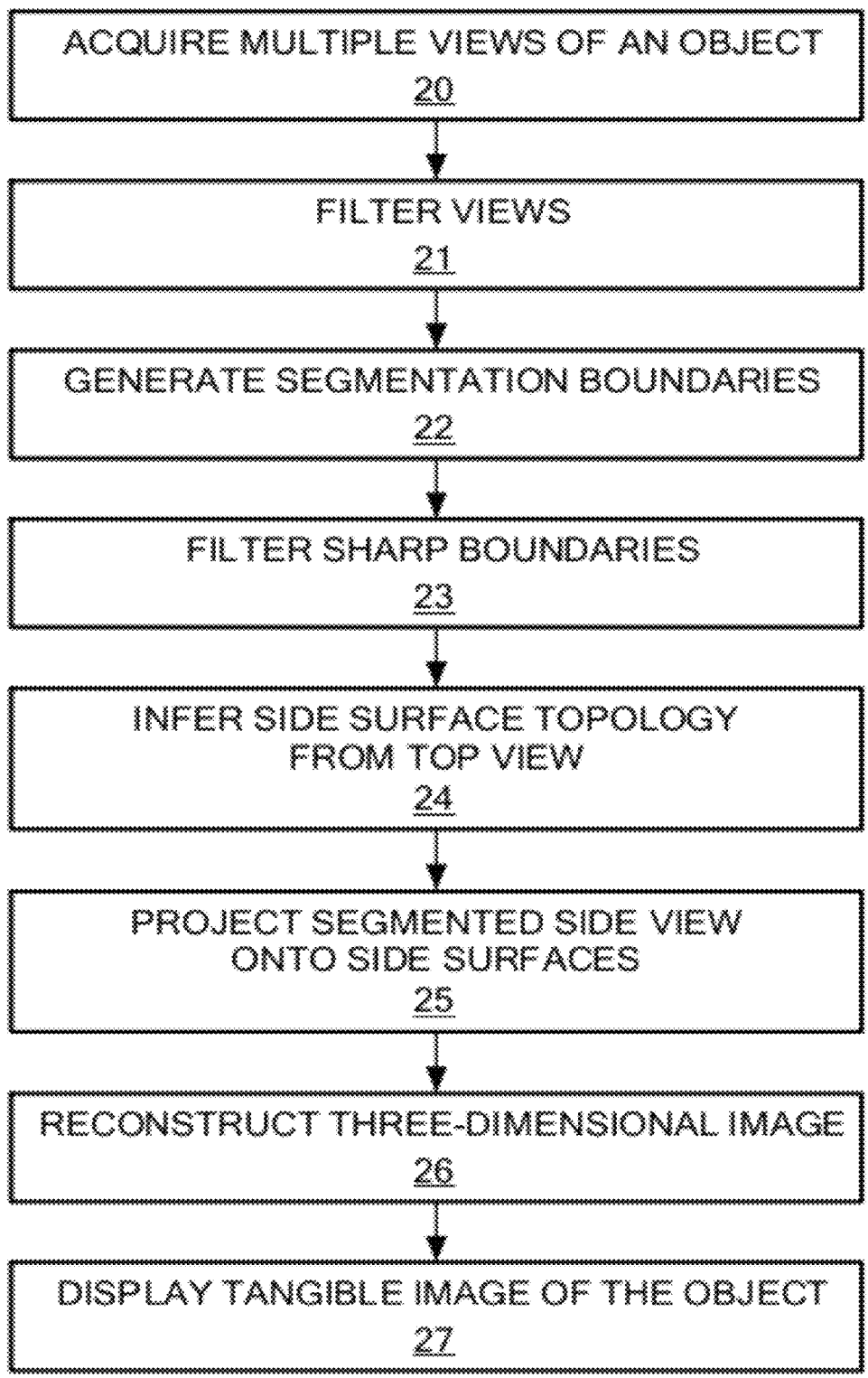
FIG. 2 is a flowchart depicting steps in the acquisition and display of a three-dimensional image, in accordance with embodiments of the present invention.
Figure 3B:
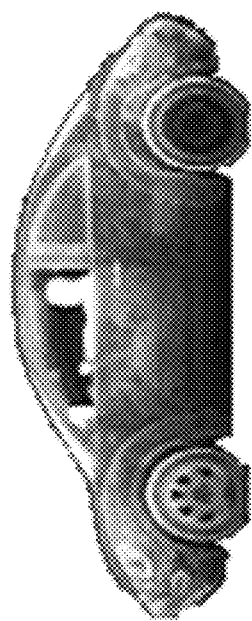
FIGS. 3($a$)-3($d$) depict results of image preprocessing steps, in accordance with an embodiment of the present invention.
Figure 3D:
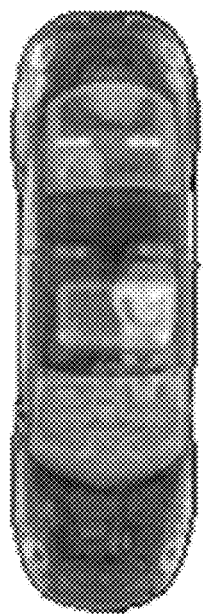
Figure 3A:
Figure 3C:
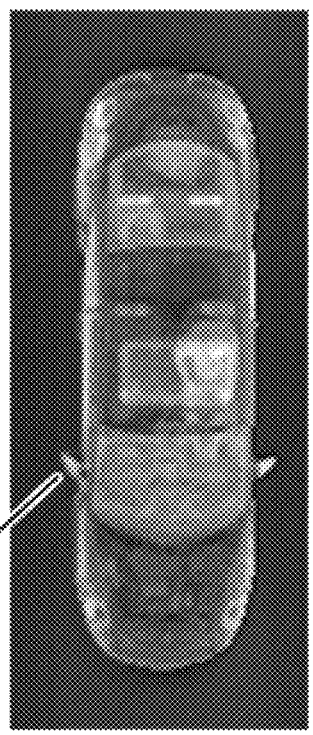

As now described with reference to the flowchart of FIG. 2 and the images of FIGS. 3(*a*)-2(*d*), processes in accordance with embodiments of the invention segment and register multiple images, as follows. A plurality of views 30 of object 15 (shown in FIG. 1) are acquired 20 and preliminarily processed 21, to include filtering, averaging, etc. A subsequent segmentation process 22 generates segmentation boundaries. Sharp edges 34 in the segmentation boundary in a first view 30 (here, a side view) are preferably filtered out 23 since they are likely to be caused by noise and they distort the 3D surface mapping. This is illustrated in FIGS. 3(*a*) and 3(*b*). In an analogous set of steps, a second view 32 (here, a top view) with segmentation is also refined to filter out sharp boundary edges, as illustrated in FIGS. 3(*c*) and 3(*d*).

In accordance with alternate embodiments of the invention, mirrors 36 may be removed from top views of a car.

Views obtained of the left and right sides of an inspected object lack information on the topology of the side surfaces of the vehicle. Views obtained by each of backscatter modules 17 and 18 are each characterized by a respective view planes, onto which the respective scatter images are effectively projected.

Figure 4:
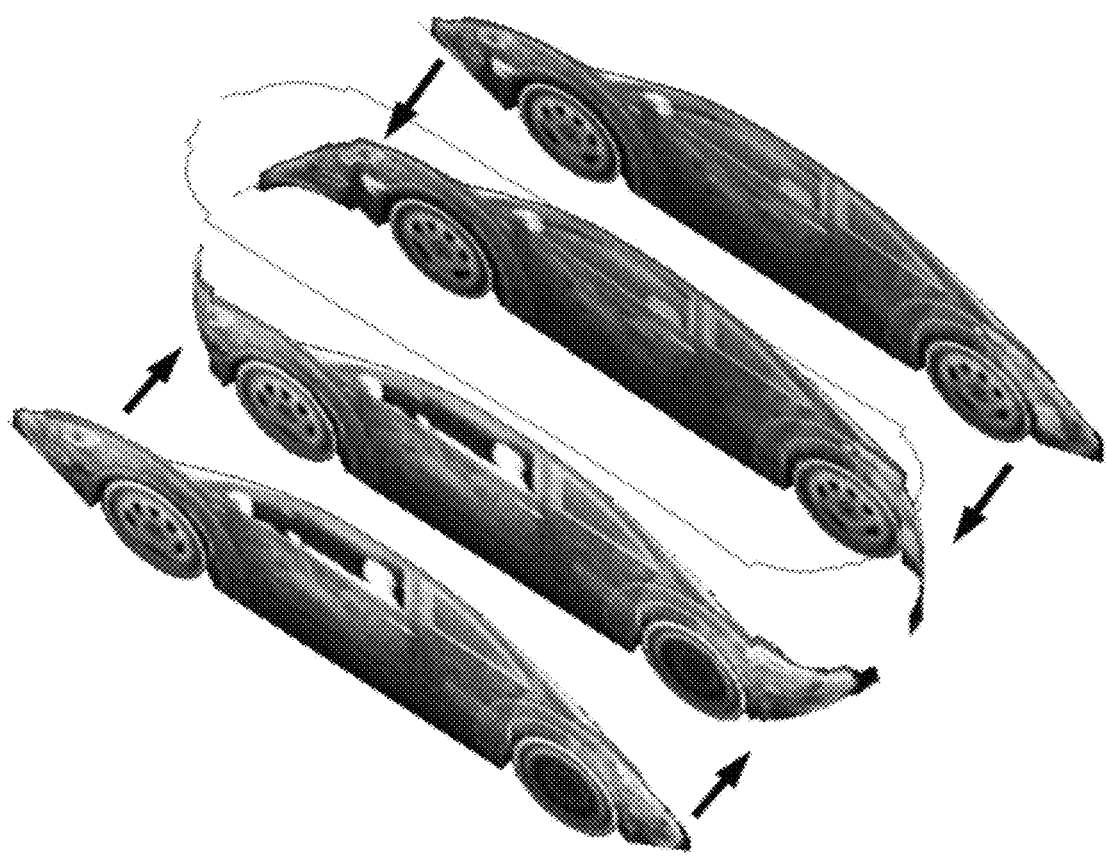
FIG. 4 depicts a process of inferring a side view from a top view, in accordance with an embodiment of the present invention.

Side surfaces are derived in step 24, however, in accordance with the present invention, from the top view as illustrated in FIG. 4. The top view provides information with respect to a dimension transverse to the respective view planes of the side-looking scatter images. Derivation of surface topologies is taught, for example, in Benosman et al. (eds.), "Panoramic Vision: Sensors, Theory, and Applications", (2001), which is incorporated herein by reference. This allows projection 25 of the segmented side views onto these surfaces, as illustrated in FIG. 4.

Figure 5:
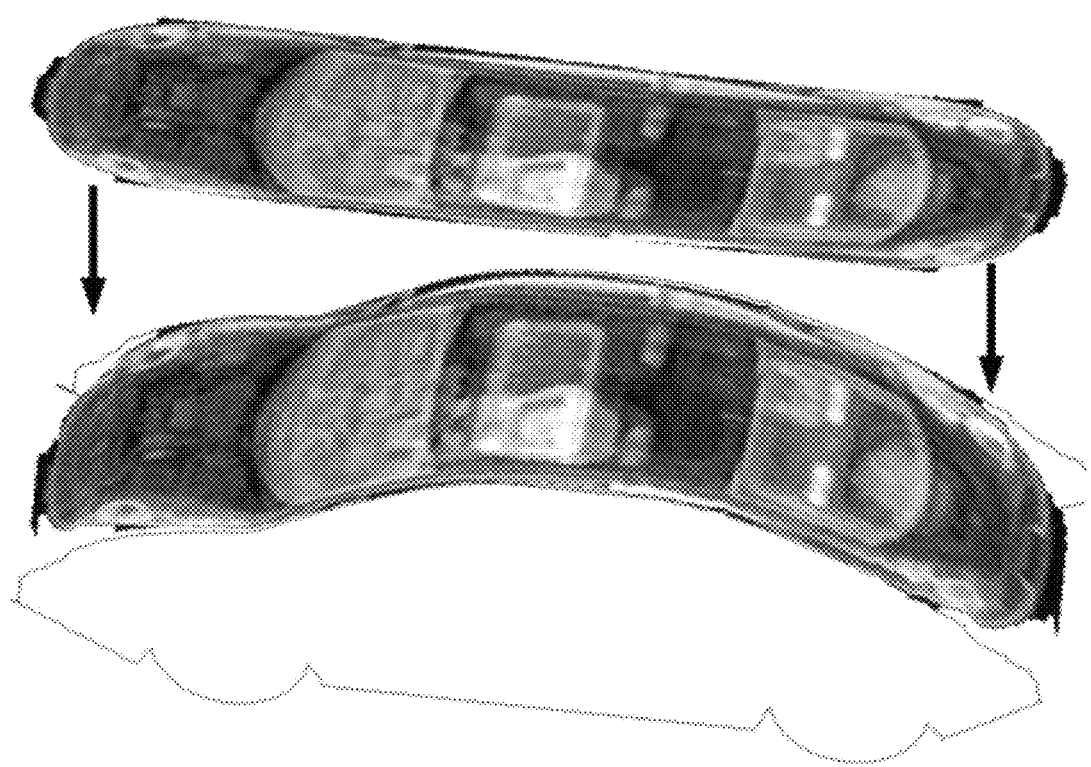
FIG. 5 depicts a process of inferring a top view from one or more side views, in accordance with a further embodiment of the present invention.

Similar to the side views, the top view does not have surface information built into it, but that information can be inferred from the side views as illustrated in FIG. 5.

Figure 6:
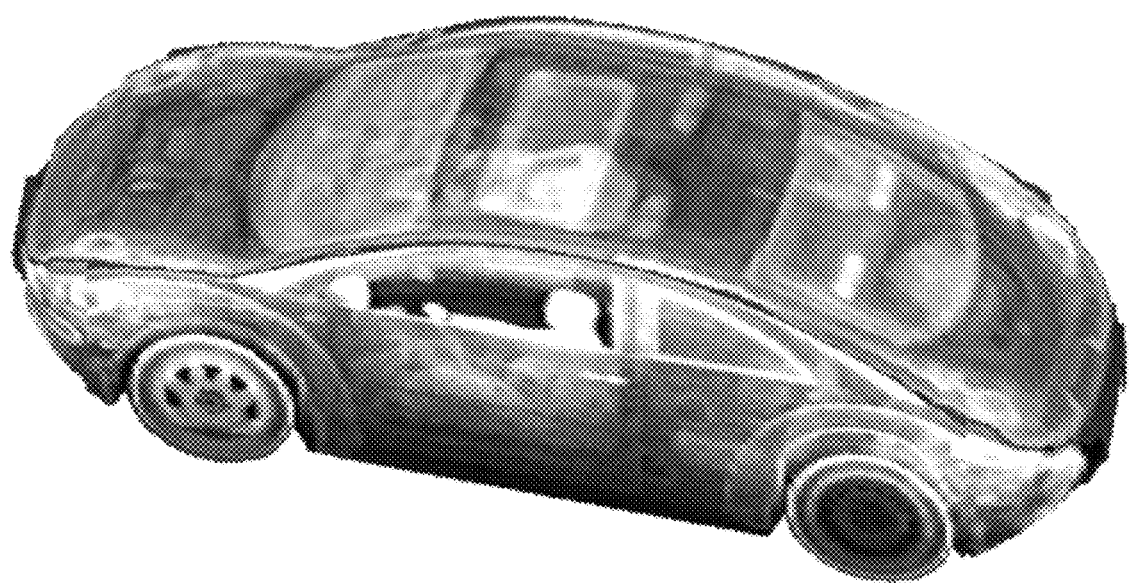
FIG. 6 depicts a 3D surface, for display as a tangible image in accordance with embodiments of the present invention.

Finally, the images from the three sides are stitched together, in step 26, as illustrated in FIG. 6. Stitching is performed using techniques described in detail, for example, in Benosman et al. (2001). Once a three-dimensional surface has been reconstructed, it is displayed 27 as a tangible image on a display monitor, so that it may be viewed by a human operator.

The brightness of an object is inversely proportional to the distance between the object and the backscatter detectors. This property does not hold true in X-ray transmission images. For example, examining the driver side backscatter image, the driver appears brighter (and bigger) than the passenger next to him. This is very similar to what is captured by a photographic camera or a human eye. Thus, the 3D surface mapping is similar to what a human expects to see, making the images easier to interpret.

Backscatter image 3D surface projection methods such as described herein can also be applied to systems designed to scan personnel, such as AS&E's SmartCheck™ system. In accordance with this embodiment of the invention, body scan images from pre-calibrated front, back, and side views are processed in the same way as for vehicles and projected on to one or more standard human body 3D surfaces, based on control-point pairs. By always presenting the backscatter image information (regardless of actual body shape or size) on a few select 3D surfaces, important threat information is still available to the inspector, while also protecting passenger privacy. The technique also allows for the rotation of the image, allowing for easier interpretation of the image data.

Once a 3D surface, such as that shown in FIG. 6, is created, the user may change the viewing angle that appears as a tangible image displayed on a display monitor, by simply moving a mouse or other user input, all as well known in the art. For convenience, an optimized preset viewing angle is initially chosen for the viewer.

The disclosed methods for creating a three-dimensional surface reconstruction of an inspected object based on scattering of penetrating radiation may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The described embodiments of the invention are intended to be merely exemplary and numerous variations and modifications will be apparent to those skilled in the art. All such variations and modifications are intended to be within the scope of the present invention as defined in the appended claims.

We claim:

1. A method for creating a tangible image of an inspected object, the method comprising:
    illuminating the object with a first source of penetrating radiation, the first source of radiation generating a pencil beam that penetrates the inspected object to a significant depth and that defines a first viewing point;
    illuminating the object with a second source of penetrating radiation, the second source of radiation generating a pencil beam that penetrates the inspected object to a significant depth and that defines a second viewing point;
    detecting post-interaction penetrating radiation due to the first source and generating a first signal based on a first view of the object, characterized by a first view plane, of the inspected object;
    detecting post-interaction penetrating radiation due to the second source and generating a second signal based on a second view of the inspected object;
    deriving information with respect to a dimension transverse to the first view plane based on the second signal; and
    displaying a tangible image of the inspected object depicting information with respect at least to the first view plane and the transverse dimension.

2. A method in accordance with claim 1, further comprising:
    segmenting the first view of the object.

3. A method in accordance with claim 1, wherein the step of illuminating includes illuminating with x-ray radiation.

4. A method in accordance with claim 1, further comprising:
    constructing a three-dimensional surface of the object for display as the tangible image.

5. A method in accordance with claim 1, wherein the object is a vehicle.

6. A method in accordance with claim 1, wherein the object is a person.

* * * * *